(12) United States Patent
Wei et al.

(10) Patent No.: US 8,747,812 B2
(45) Date of Patent: Jun. 10, 2014

(54) AQUEOUS NEGATIVE CONTRAST MEDIUM FOR CT IMAGING OF THE GASTROINTESTINAL TRACT AND THE PREPARATION METHOD THEREOF

(76) Inventors: Xiaohui Wei, Shanghai (CN); Jianrong Xu, Shanghai (CN); Yuhong Xu, Shanghai (CN)

(*) Notice: Subject to any disclaimer, the term of this patent is extended or adjusted under 35 U.S.C. 154(b) by 966 days.

(21) Appl. No.: 12/300,240

(22) PCT Filed: May 22, 2006

(86) PCT No.: PCT/CN2006/001063
§ 371 (c)(1),
(2), (4) Date: Nov. 10, 2008

(87) PCT Pub. No.: WO2007/131390
PCT Pub. Date: Nov. 22, 2007

(65) Prior Publication Data
US 2010/0166668 A1    Jul. 1, 2010

(30) Foreign Application Priority Data

May 11, 2006    (CN) .......................... 2006 1 0026434

(51) Int. Cl.
*A61K 49/04* (2006.01)
(52) U.S. Cl.
CPC ......... *A61K 49/0409* (2013.01); *A61K 49/0457* (2013.01)
USPC ........................................................ 424/9.4
(58) Field of Classification Search
None
See application file for complete search history.

(56) References Cited

U.S. PATENT DOCUMENTS

| | | | | |
|---|---|---|---|---|
| 5,562,099 A | * | 10/1996 | Cohen et al. | 600/458 |
| 6,783,752 B2 | * | 8/2004 | Østensen et al. | 424/9.52 |
| 2003/0053953 A1 | * | 3/2003 | Unger | 424/9.52 |

FOREIGN PATENT DOCUMENTS

CN    1233505 (A)    11/1999

OTHER PUBLICATIONS

Abstract—Wei, et al., "The Prospective Study on a Contrast Medium Eliminating Artifact Produced by Endogastric Fluid Level in CT Scan", Journal of Practical Radiology, (1997), 03.

* cited by examiner

*Primary Examiner* — Brian Gulledge
(74) *Attorney, Agent, or Firm* — Dority & Manning, PA

(57) ABSTRACT

An aqueous negative contrast agent for CT imaging of the gastrointestinal tract and the preparation method thereof. The agent is used in biological and pharmaceutical field. Its components and the weight percent are: hydrogel matrix 0.01-1%, micro-/nano-particles of the materials with low densities 5-50%, stabilization agents 0.1-5%, the rest is deionized water. The preparation method is: stabilization agents are added into the hydrogel matrix made of natural or synthetic hydrophilic polymers, then micro-/nano-particles of the materials with low CT densities are added or prepared, and uniformly dispersed in the hydrogel matrix. The CT density of the resulted aqueous negative contrast agent for CT imaging of the gastrointestinal tract is −30 HU to −500 HU. It can decrease the CT density inside the intestine lumen to lower than −30 HU. The intestine wall can be depicted clearly and the CT signals intensities inside lumen are uniform. It is feasible for 3D images processing such as virtual endoscopy reconstruction with the negative contrast agent. The agent is safe, stable and nontoxic. It will not lead to diarrhea after administration. It is of great significance for the improved sensitivity and specificity of CT diagnosis for the diseases on the intestinal wall and lumen.

17 Claims, No Drawings

AQUEOUS NEGATIVE CONTRAST MEDIUM FOR CT IMAGING OF THE GASTROINTESTINAL TRACT AND THE PREPARATION METHOD THEREOF

CROSS-REFERENCE TO RELATED APPLICATIONS

This application claims priority to Chinese Application No. CN200610026434.4 filed May 11, 2006, and International Application Serial No. PCT/CN2006/001063 filed May 22, 2006.

FIELD OF INVENTION

The invention relates to a contrast agent and the preparation method thereof. Particularly, the invention relates to an aqueous negative contrast agent for CT imaging of the gastrointestinal tract and the preparation method thereof. The invention is in the biomedical field.

BACKGROUND OF THE INVENTION

Diseases originated in the gastrointestinal tract (GI tract), especially malignant tumors such as the colon cancers, pose daunting threats to human health. Computed Tomography (CT) is widely used for the medical imaging diagnosis of GI tract diseases. In recent years, with the application of the multi-planar spinal CT instrument with scanning speed at sub-second range, the GI imaging qualities have greatly improved with much fewer artifacts resulted from breathing and intestine peristalsis. Therefore CT plays a more and more important role in the diagnosis of GI tract, especially colon, diseases. In current clinical practice, air and water are usually used for the filling of the intestine to fully display of the anatomic structures, in order to improve the detection accuracy and reduce false positives. In addition, CT virtual endoscopy techniques for three dimension (3D) image reconstruction and analysis were developed to further improve the diagnostic specificity and sensitivity for GI tract diseases. But the early and accurate detection of colon tumors that originated at the colon wall was still not possible by CT imaging only. The most important reason for such a limitation is that imaging contrast agents currently available are either positive contrast agents (with high CT densities) or neutral contrast agents (with CT densities similar to that of water). However, the positive contrast agents tended to conceal the small changes on the intestinal wall, and the high CT density in the lumen may interfere with the colon wall images. The neutral contrast agents could not show clearly the anatomical structures of the intestinal wall, intestinal lumen and related tissues, because their CT densities are not much different from the wall, so the contrast is low even with full filling of the colon. There is usually a high missing rate in diagnosis. Besides, the poor contrast images can't be used for virtual endoscopy reconstruction (VE and VR) and analysis. Therefore, the development of negative CT contrast agent (with low CT density) is needed for clearer intestinal wall visualization, and 3D virtual endoscopy reconstruction and analysis.

Up to date, there is no such negative contrast agent available clinically that can satisfy all three requirements in CT imaging for the GI tract: good filling of the intestine, clear visualization of the intestinal wall and feasible for 3D virtual endoscopy. There were some reports proposing the use of plant cellulose, milk, emulsion, and paraffin to be used as the negative CT contrast agents. The CT densities of the plant cellulose, milk and fat emulsion are in the range of 10 to −80 Hounsfield Unit (HU), which is not low enough for clear visualization of the intestinal wall and the 3D virtual endoscopy reconstruction. The CT density of paraffin is around −100 HU. It is useful for the better depiction of the intestinal wall and 3D virtual endoscopy reconstruction, but severe diarrhea resulting from the administration of paraffin restricts its clinical application. Air filling is widely used in clinical practices to serve as a kind of negative contrast medium. It has the CT density of −1000 HU, which is optimal for 3D virtual endoscopy reconstruction and can detect extruding features in the lumen such as polyps or tumors with higher sensitivity and specificity, but the depiction of the intestinal wall in the transverse images is poor because of the air/water interface distortion. The thickness of the intestinal walls looks much thinner, so it is very hard to find any pathological changes on the intestinal wall.

Technological literature searches show that the only contrast agent that has been used in the clinic and actually improved the CT visualization of the intestinal wall was the Mucofalk suspension made of the swelling plantain seeds. (Helical CT of the small bowel with an alternative oral contrast material in patients with Crohn disease, Doerfler O C, Ruppert-Kohlmayr A J, Reittner P, et al, ABDOMINAL IMAGING, 2003, 28(3): 313), but the CT density difference between the intestinal wall and the lumen is still not large enough for 3D virtual endoscopy.

OBJECT AND SUMMARY OF THE INVENTION

The present invention addresses the problems and limitations of the contrast agents currently available for CT imaging of the intestinal tract and provides an aqueous negative contrast agent for CT imaging of the gastrointestinal tract and the preparation method thereof. The suspension type contrast agent is safe, nontoxic and stable. It contains no paraffin or vegetable oil or other materials such as mannitol that may lead to diarrhea. The intestine can be well distended with the negative contrast agent, and the intestinal wall can be clearly visualized. 3D virtual endoscopy is also feasible. So, the CT imaging sensitivity and the specificity of the detection of pathological changes on the intestinal wall and in the intestinal lumen are greatly improved. More reliable radiographic readings can be provided for the clinical diagnosis and analysis. In addition, the aqueous negative contrast agent is convenient for administration. After a single bowel preparation, a series of CT scans can be carried out. Thus, the agent can reduce the cost and the inconvenience of a patient for bowel preparation.

The present invention is realized through the following technical solutions:

The aqueous negative contrast agent for CT imaging of the gastrointestinal tract of the present invention is a suspension composed of micro-/nano-particles of low density materials suspended in hydrogel matrix. The components of the negative contrast agent and their weight percent compositions are: hydrogel matrix 0.01-1%, micro-/nano-particles of low density materials 5-50%, stabilization agents 0.1-5%, the rest is deionized water. The said micro-/nano-particles of low density materials are gas microbubbles and/or solid particles with low densities.

The contrast agent of the present invention has the CT density in the range of −30 HU to −500 HU. The contrast agent can substantially decrease the CT density inside the intestine lumen to be significantly lower than that of the intestinal wall after the full filling of the intestine, without disuniformity in the density dispersion. The matrix of the contrast agent of the present invention is formulated into viscous solutions or semisolids by using natural or synthetic hydrophilic polymers dispersed or swelled in water. The negative contrast agent is capable of achieving full distention of intestine but at the same time maintain good fluidity.

The present invention also provides the preparation method of the aqueous negative contrast agent for CT imaging of the gastrointestinal tract. The detailed method is: first, disperse or swell the natural or synthetic hydrophilic polymers in water to obtain the hydrogel matrix. Then, the micro-/nano-particles of the low density materials plus stabilizing agents are added or prepared, and dispersed in the hydrogel matrix to obtain a suspension in the hydrogel matrix. By selecting different stabilization agents and varying the viscosities of the hydrogels, we could improve the stability and the fluidity of the suspensions. The negative contrast agent with good uniformity, stability and fluidity that meets the requirement for the research of CT imaging of intestinal tract is prepared.

The low density materials used in this invention refer to materials that have densities smaller than that of water, with the intrinsic CT densities in the range of −50 HU to −1000 HU. They may be easily dispersed in water but not be soluble in water. The materials include: gas microbubbles, polyethylene (PE) particles for medical use, polypropylene (PP) particles for medical use and the mixtures composed of the gas microbubbles, PE and PP particles mentioned above. The concentration of the micro-/nano-particles of the materials with low densities in the suspension can be changed according to the requirement in using the agent. Generally, the concentration is 5-50%.

The gas microbubbles described in the present invention refer to gas microbubbles at 25° C. under one atmosphere pressure. The gases include air, carbon dioxide, nitrogen, oxygen, fluoroalkanes, chlorofluoroalkanes, thiofluoroalkanes and inert gases including helium, neon, argon, krypton, xenon, and their combinations. The volume concentration of the gaseous microbubbles in the hydrogel matrix is 5-50% at 25° C. under one atmosphere pressure.

The low CT density solid particles described in the present invention refer to water-insoluble polymers particles that have smaller densities than that of water at 25° C. under one atmosphere pressure, which have the intrinsic CT densities in the range of −50 HU to −1000 HU. The materials include polyolefin, polyethylene, polypropylene, their mixed polymers, and the combinations thereof. The diameters of the particles are in the range of 0.05 microns to 1000 microns. The concentration in the hydrogel matrix is 5-50%.

The hydrogel matrix used in the present invention may be any type of the accepted natural and synthetic hydrophilic polymers in this technical field. The polymers include: cellulose and the derivatives thereof, chitosan and the derivatives thereof, agar, gelatin, arabic gum, tragacanth, sodium polyacrylate and their combinations. The concentration of the hydrogel is 0.01-1%. Stabilization agents should be further added into the suspension to increase the stability of the suspension, and to achieve a more uniform dispersion of the particles of the materials with low densities inside the suspension.

The stabilization agents used in the present invention are selected from proteins, caprolactone gluconate, ionic and nonionic surfactants, lipids, amphiphilic polymers and their combinations in different ratios. The examples are sodium dodecylsulphonate, sorbitol fatty acid ester, sorbitan fatty acid ester, copolymers of polyoxyethylene and polyoxypropylene (PEO-PPO) and their combinations. The concentration of the stabilization agents in the suspension is 0.1-5%.

There are two different methods for the generation of the suspensions of gaseous microbubbles with low densities in the hydrogel matrix. In one embodiment, gases, such as air, nitrogen and inert gases are fed into the hydrogel matrix that contains stabilization agents in suitable concentrations, to generate gaseous microbubbles with high speed stirring. The gaseous microbubbles are further dispersed and stabilized with the aid of the stabilization agents in the hydrogel matrix. In another embodiment, liquids with low boiling points, such as fluoroalkane, chlorofluoroalkane and thiofluoroalkane and their mixtures, are emulsified into the hydrogel at the temperatures below the phase-transition temperatures to form an oil-in-water emulsion. The gas microbubbles coated with the stabilization agents are generated by heating the oil-in-water emulsion.

The suspensions of the low CT density material particles in the hydrogel matrix are prepared by any of the three following preparation methods. In one embodiment, the pre-frozen solid particles of polyethylene or polypropylene for medical use were loaded into a jet pulverizer for micronization. The resulted fine solid particles in diameters of 0.05-1000 microns are further mixed with the stabilization agents, and dispersed into the hydrogel matrix to get suspensions with different CT densities. In another embodiment, the solid particles of polyethylene or polypropylene for medical use are mixed with the stabilization agents, then pre-freeze. The mixtures are put into a jet pulverizer for micronization. The resulted find solid particles with hydrophilic surfaces in the diameters of 0.005-1000 microns are then dispersed into hydrogel matrix to get suspensions of solid particles with low densities. In another embodiment, the stabilization agents were dissolved in organic solvents, and sprayed onto the surfaces of the solid particles of polyethylene or polypropylene for medical use. Solid granules are resulted by granulation and removal of the organic solvents. The suspensions with different low CT densities are prepared by dispersing the solid granules into the hydrogel matrix instantly prior to administration.

The aqueous negative contrast agent for CT imaging of the intestinal tract as prepared in the present invention is of good uniformity, stability and fluidity. It can effectively increase the definition and contrast of the intestinal wall images. Gaseous microbubbles and/or solid particles with low densities are uniformly dispersed in the suspensions without separation. In addition, the negative contrast agent has good fluidity, which meets the requirement for clinical enema administration. In experiments using ex vivo pig small intestines and in Beagle dogs gastrointestinal tract imaging studies, the aqueous negative contrast agent were shown to greatly decrease the CT density of the intestine lumen to as low as −30 HU to −200 HU. Because the CT density of the outside abdomen cavity is around −100 HU to −150 HU, the definition, integrity and smoothness of the intestine walls shown in the CT images using the aqueous negative contrast agent are much better than that in the control group using water instead of the agent of the present invention. Besides, the signals in the intestine lumens are uniform. No signal differences resulted from the suspending particles' aggregation or separation. These further enhance the reliability of the imaging diagnosis.

The aqueous negative contrast agent for CT imaging of the intestinal tract as prepared in the present invention can at the same time solve the problems on the 2D intestine wall depiction and 3D virtual endoscopy reconstruction. Thus, the sensitivity and specificity for imaging diagnosis of diseases originating from the intestine wall and lumen are greatly improved. This is especially of significance for the early reliable detection of the malignant tumors such as colon cancer. Hydrogel is used as the matrix for the negative contrast agent. It can distend the intestine well, and eliminate the severe diarrhea resulted from the administration of oils, fats or mannitol. The gaseous microbubbles and/or solid particles with low densities are safe and non-irritant. They can effectively decrease the CT density of the lumen after fulfillment of the intestine. The materials for the preparation of the aqueous negative contrast agent are commonly available. The preparation method is simple and easy to be scaled up. According to the different imaging request, the CT density of the aqueous negative contrast agent can be easily adjusted by changing the added amount of the materials with low CT densities in the hydrogel matrix for clear 2D intestine wall depiction and good 3D images reconstruction.

The examples according to the present invention are as follows, which further illustrate the technical solution of the present invention.

EXAMPLE 1

In this example, the main components of the contrast agent are: polyethylene particles for medical use in mean diameter of 200 microns prepared by ultra-fine milling account for 20%, the mixture of Pluronic F68 and sodium dodecylsulphonate as the stabilization agent account for 5%, 0.01% sodium polyacrylate as the hydrogel matrix, the rest is deionized water. The preparation method is: commercial available polyethylene particles for medical use and Pluronic F68 are mixed in the ratio of 100:1, then transferred to jet pulverizer for ultra-fine milling. Polyethylene particles surface adsorbed with Pluronic F68 in the mean diameter of 200 microns are resulted. 20 g resulted polyethylene particles and 5 g stabilization agent (the mixture of 1 g SDS and 4 g Pluronic F68) are mixed in a mortar. Then, 20 ml sodium polyacrylate (with Mw higher than 300,000) solution in the concentration of 0.05% is added into the mortar, and mixed well. Deionized water is added into the mortar until the total weight of the suspension reaches 100 g. The suspension is transferred to a flat-bottom beaker, and further blended using magnetic stirring in medium speed. Uniform suspension with polyethylene particles suspended in sodium polyacrylate hydrogel matrix is obtained.

The measurement of the CT density of the contrast agent: the prepared suspension is filled to plastic tubes with caps, and CT scanning is performed for the measurement of its CT density. The measurement results indicate that: in the control group, the CT density of water keeps zero; the CT density of the prepared negative contrast agent suspension is −30 HU. There is no significant difference in the CT densities among different scanning layers. The suspension keeps stable for 20 min without separation.

The measurement of the intestine lumen CT densities in ex vivo pig intestines: the prepared suspension is filled to a piece of the ex vivo pig intestine with one end tied. The air rested in the intestine is removed, and the other end is tied. Water is filled into another piece of the ex vivo pig intestine as the control using the same protocol. The two pieces of the ex vivo pig intestines are immersed in paraffin or vegetable oil that simulate the in vivo outluminal tissues in human. This is also helpful to eliminate the interference on the measurement from the partial volume artifacts of gas. CT scanning is performed and the CT densities of the intestine lumens are measured. The results are: the CT density of the intestine lumen in the control group (water group) is around 0 HU, and the intestine wall depiction is poor; the CT density of the intestine lumen in the study group (the aqueous negative contrast agent group) is around −30 HU, and the intestine wall depiction is better than the control group. The signal densities inside the lumen are uniform.

EXAMPLE 2

In this example, the main components of the contrast agent are: polyethylene particles for medical use in mean diameter of 10 microns prepared by co-milling account for 50%, the mixture of Pluronic F68 and SDS as the stabilization agent account for 3.5%. 0.005% sodium polyacrylate and 0.03% methylcellulose are used as the hydrogel matrix. The rest is deionized water. The preparation method is: the polypropylene particles for medical application with CT density of −200 HU sieved through 40-mesh sifter are mixed with Pluronic F68 in the ratio of 100:1, and frozen. The mixture is then co-milled by an air miller to get polypropylene particles with hydrophilic surface in the mean diameter of 10 microns. 50 g resulted polypropylene particles and 3.5 g stabilization agent (the mixture of 0.5 g SDS and 3 g Pluronic F68) are mixed in a mortar. Then, 0.05% sodium polyacrylate solution and 0.3% methyl cellulose solution both in 10 ml are added into the mortar, and mixed well. Deionized water is added into the mortar until the total weight of the suspension reaches 100 g. The suspension is further blended using magnetic stirring. The CT density of the resulted aqueous negative contrast agent with polypropylene particles suspended therein is measured using the method as described in example 1, as well as the pig intestine lumen CT density after filling with the agent. The results are: the CT density of the prepared aqueous negative contrast agent is around −100 HU; the CT density of the pig intestine lumen is decreased to as low as −100 HU. The intestine wall in integrity is visualized clearly and smoothly. The signals intensities inside the lumen are uniform without visible conglomeration in the CT images.

EXAMPLE 3

In this example, the main components of the contrast agent are: polypropylene particles for medical use in mean diameter of 1000 microns account for 35%, the mixture of Pluronic F68 and sodium dodecylsulphonate as the stabilization agent account for 4.8%. 0.005% agar and 0.02% methylcellulose are used as the hydrogel matrix. The rest is deionized water. The preparation method is: 100 g ultra-fine milled PP particles for medical use in the mean diameter of 1000 microns with CT density of −100 HU are put into a coating pan. 6% Pluronic F68 ethanol solution is uniformly sprayed onto the surface of the PP particles. The polypropylene particles coated with Pluronic F68 are taken out, dried at 60° C. and weighed. The Pluronic F68 coated on the polypropylene particles surface account for 2% (of the polypropylene particles weight). 35 g dried polypropylene particles and 4 g stabilization agent (the mixture of 0.5 g sodium dodecylsulphonate and 3.5 g Pluronic F68) are mixed in a mortar. Then, 0.05% agar solution, 0.2% methyl cellulose solution both in 10 ml, and adequate deionized water are added into the mortar, then mixed well. Deionized water is added into the mortar until the total weight of the suspension reaches 100 g. The suspension is further blended using magnetic stirring in medium speed. The CT density of the resulted aqueous negative contrast agent with polypropylene particles suspended therein is measured using the method as described in example 1, as well as the pig intestine lumen CT density after filling with the agent. The results are: the CT density in the intestinal lumen is reduced around −85 HU after filling with the agent; the CT density of the pig intestine lumen is decreased to as low as −85

HU. The intestine wall in integrity is visualized clearly and smoothly. The signals intensities inside the lumen are uniform without visible conglomeration in the CT images.

EXAMPLE 4

In this example, the main components of the contrast agent are: fine powders of polyethylene and polypropylene mixture for medical use in mean diameter of 50 nanometer account for 5%, the mixture of the block copolymer of PEO-PPO and egg lecithin as the stabilization agent account for 2%, 0.5% tragacanth as the hydrogel matrix, the rest is deionized water. The preparation method is: particles of polyethylene and polypropylene mixture for medical use, the PEO-PPO block copolymer and egg lecithin are mixed in the ratio of 50:1:1, then transferred to jet pulverizer for ultra-fine milling. Fine powders of polyethylene and polypropylene mixture with the stabilization agents adsorbed on the surface in the mean diameter of 50 nanometer are resulted. The CT density of the resulted fine powders of polyethylene and polypropylene mixture is −1000 HU. 5 g resulted polyethylene and polypropylene mixture fine powders and 2 g PEO-PPO block copolymer are blended with 0.5% tragacanth solution to form a suspension. Deionized water is added into the suspension until the total weight of reaches 100 g. The CT density of the resulted aqueous negative contrast agent is measured using the method as described in example 1, as well as the pig intestine lumen CT density after filling with the agent. The results are: the CT density of the prepared aqueous negative contrast agent is around −200 HU; the CT density of the pig intestine lumen is decreased to as low as −200 HU. The intestine wall in integrity is visualized clearly and smoothly. The signals intensities inside the lumen are uniform without visible conglomeration in the CT images.

EXAMPLE 5

In this example, the main components of the contrast agent are: fine powders of the ethylene-propylene random copolymer in mean diameter of 500 nanometer account for 10%, the mixture of cremophor RH and Tween as the stabilization agent account for 3%, 0.2% arabic gum as the hydrogel matrix, the rest is deionized water. The preparation method is: particles of ethylene-propylene random copolymer, cremophor RH and Tween 60 are mixed in the ratio of 100:1:1, then transferred to jet pulverizer for ultra-fine milling. Fine powders of ethylene-propylene random copolymer with the stabilization agents cremophor RH and Tween adsorbed on the surface in the mean diameter of 100 nanometer are resulted. The CT density of the resulted fine powders of ethylene-propylene random copolymer is −600 HU. 10 g resulted fine powders of ethylene-propylene random copolymer, 1 g cremophor RH and 2 g Tween are blended with 0.2% arabic gum solution to form a suspension. Deionized water is added into the suspension until the total weight of reaches 100 g. The CT density of the resulted aqueous negative contrast agent is measured using the method as described in example 1, as well as the pig intestine lumen CT density after filling with the agent. The results are: the CT density of the prepared aqueous negative contrast agent is around −100 HU; the CT density of the pig intestine lumen is decreased to as low as −100 HU. The intestine wall in integrity is visualized clearly and smoothly. The signals intensities inside the lumen are uniform without visible conglomeration in the CT images.

EXAMPLE 6

In this example, the main components of the contrast agent are: fine powders of the ethylene-propylene block copolymer in mean diameter of one micron account for 40%, the mixture of cremophor RH, Tween and Span as the stabilization agent account for 5%, 0.8% sodium carboxymethyl cellulose (CMC-Na) as the hydrogel matrix, the rest is deionized water. The preparation method is: particles of ethylene-propylene block copolymer, cremophor RH, Tween and Span are mixed in the ratio of 100:1:2:1, then transferred to jet pulverizer for ultra-fine milling. Fine powders of ethylene-propylene block copolymer with the stabilization agents adsorbed on the surface in the mean diameter of one micron are resulted. The CT density of the resulted fine powders of ethylene-propylene block copolymer is −400 HU. 40 g resulted fine powders of ethylene-propylene block copolymer, 1 g cremophor RH, 2 g Tween and 2 g Span are blended with 0.8% CMC-Na solution to form a suspension. Deionized water is added into the suspension until the total weight of reaches 100 g. The CT density of the resulted negative contrast agent of propylene-methylcellulose hydrogel is measured using the method as described in example 1, as well as the pig intestine lumen CT density after filling with the agent. The results are: the CT density of the prepared aqueous negative contrast agent is around −80 HU; the CT density of the pig intestine lumen is decreased to as low as −80 HU. The intestine wall in integrity is visualized clearly and smoothly. The signals intensities inside the lumen are uniform without visible conglomeration in the CT images.

EXAMPLE 7

In this example, the main components of the contrast agent are: air microbubbles generated via high speed stirring account for 20% (v/v), the mixture of albumin and caprolactone gluconate as the stabilization agent account for 0.1%, methylcellulose hydrogel in the concentration of 0.4%, agar hydrogel in the concentration of 0.1% and gelatin hydrogel in the concentration of 0.05%, the rest is deionized water. The air microbubbles are stabilized by the combination with the stabilization agent in the hydrogel matrix. The preparation method is: 0.1 g stabilization agent (0.05 g albumin and 0.05 g caprolactone gluconate) is added into 100 ml hydrogel composed of 0.4% methylcellulose, 0.1% arga and 0.05% gelatin, and mixed well. Milky air microbubbles-hydrogel suspension is prepared by vigorous stirring using a homogenizer at the speed of 10000 rpm for 5 min. The CT density of the resulted aqueous negative contrast agent is measured using the method as described in example 1, as well as the pig intestine lumen CT density after filling with the agent. The results are: the CT density of the prepared aqueous negative contrast agent is around −200 HU; the CT density of the pig intestine lumen is decreased to as low as −200 HU. The signals intensities inside the lumen are uniform without visible conglomeration in the CT images.

EXAMPLE 8

In this example, the main components of the contrast agent are nitrogen microbubbles account for 50% (v/v), the mixture of albumin, cetyltrimethyl ammonium bromide (CTAB) and PEO-PPO block copolymers as the stabilization agent account for 1.55%, chitosan hydrogel in the concentration of 0.5%, gelatin hydrogel in the concentration of 0.5%, the rest is deionized water. The nitrogen microbubbles generated via high speed stirring under nitrogen stream feeding are stabilized by the combination with the stabilization agent in the suspension. The preparation method is: 1.55 g stabilization agent (1 g albumin, 0.05 g CTAB and 0.5 g Pluronic F68) is added into 100 ml hydrogel composed of 0.5% chitosan and 0.5% gelatin, and mixed well. Milky nitrogen microbubbles-hydrogel suspension is prepared by vigorous stirring of the solution using a homogenizer at the speed of 10000 rpm for 5 min under continuous feeding of nitrogen. The CT density of the resulted aqueous negative contrast agent is measured using the method as described in example 1, as well as the pig intestine lumen CT density after filling with the agent. The results are: the CT density of the prepared aqueous negative contrast agent is around −500 HU; the CT density of the pig intestine lumen is decreased to as low as −500 HU. The signals intensities inside the lumen are uniform without visible conglomeration in the CT images.

EXAMPLE 9

In this example, the main components of the contrast agent are helium microbubbles that account for 5% (v/v), the mixture of sodium dodecylsulphonate (SDS) and Pluronic F68 as the stabilization agent account for 1%, methylcellulose hydrogel in the concentration of 0.4%, agar hydrogel in the concentration of 0.3%, the rest is deionized water. The helium microbubbles generated via high speed stirring under helium stream feeding are stabilized by the combination with the stabilization agent in the suspension. The preparation method is: 1 g stabilization agent (0.5 g SDS and 0.5 g Pluronic F68) is added into 100 ml mixed solution composed of 0.4% methylcellulose and 0.3% agar, and mixed well. Milky helium microbubbles-hydrogel suspension is prepared by vigorous stirring of the solution using a homogenizer at the speed of 10000 rpm for 3 min under continuous feeding of helium. The CT density of the resulted aqueous negative contrast agent is measured using the method as described in example 1, as well as the pig intestine lumen CT density after filling with the agent. The results are: the CT density of the prepared aqueous negative contrast agent is around −50 HU; the CT density of the pig intestine lumen is decreased to as low as −50 HU. The signals intensities inside the lumen are uniform without visible conglomeration in the CT images.

EXAMPLE 10

In this example, the main components of the aqueous negative contrast agent are: $SF_6$ microbubbles account for 10% (v/v), the mixture of phospholipid, phosphatidic acid and Pluronic F68 as the stabilization agent account for 2%, methylcellulose hydrogel in the concentration of 0.3%, arga hydrogel in the concentration of 0.2%, the rest is deionized water. The $SF_6$ microbubbles generated via heating gasification are stabilized by the combination with the stabilization agent in the suspension. The preparation method is: 2 g stabilization agent (0.8 g Pluronic F68, 1 g phospholipid and 0.2 g phosphatidic acid) is added into 100 ml hydrogel composed of 0.3% methylcellulose and 0.2% agar, and mixed well. The solution is cooled down by ice cold bath, and $SF_6$ in liquid state is dropped in. Oil-in-water emulsion using $SF_6$ as the oil phase is prepared using a homogenizer at the speed of 10000 rpm for 1 min. The emulsion is heated by a water bath at 25° C., and $SF_6$ is gasifies to form gas microbubbles. Milky $SF_6$ microbubbles-hydrogel suspension is obtained. The CT density of the resulted aqueous negative contrast agent is measured using the method as described in example 1, as well as the pig intestine lumen CT density after filling with the agent. The results are: the CT density of the prepared aqueous negative contrast agent is around −290 HU; the CT density of the pig intestine lumen is decreased to as low as −290 HU. The signals intensities inside the lumen are uniform without visible conglomeration in the CT images.

EXAMPLE 11

In this example, the main components of the aqueous negative contrast agent are: trichlorofluoromethane microbubbles account for 30% (v/v), the mixture of phophatidylethanolamine, phosphatidic acid and Pluronic F68 as the stabilization agent account for 5%, sodium carboxymethyl cellulose (CMC-Na) hydrogel in the concentration of 0.1%, agar hydrogel in the concentration of 0.1%, the rest is deionized water. The trichlorofluoromethane microbubbles generated via heating gasification are stabilized by the combination with the stabilization agent in the suspension. The preparation method is: 5 g stabilization agent (2.5 g Pluronic F68, 2 g phosphatidylethanolamine and 0.5 g phosphatidic acid) is added into 100 ml hydrogel composed of 0.1% CMC-Na and 0.1% agar, and mixed well. The solution is cooled down by ice cold bath, and trichlorofluoromethane in liquid state is dropped in. Oil-in-water emulsion using trichlorofluoromethane as the oil phase is prepared using a homogenizer at the speed of 10000 rpm for 3 min. The emulsion is heated by a water bath at 30° C., and trichlorofluoromethane is gasified to form gas microbubbles. Milky trichlorofluoromethane microbubbles-hydrogel suspension is obtained. The CT density of the resulted aqueous negative contrast agent is measured using the method as described in example 1, as well as the pig intestine lumen CT density after filling with the agent. The results are: the CT density of the prepared aqueous negative contrast agent is around −400 HU; the CT density of the pig intestine lumen is decreased to as low as −400 HU. The signals intensities inside the lumen are uniform without visible conglomeration in the CT images.

EXAMPLE 12

In this example, the main components of the aqueous negative contrast agent are: microbubbles of the mixture of dichlorofluoroethane and trichlorofluoromethane account for 20% (v/v), the mixture of phospholipid, phosphatidylethanolamine, and Pluronic F68 as the stabilization agent account for 3%, sodium polyacrylate hydrogel in the concentration of 0.05%, agar hydrogel in the concentration of 0.1%, the rest is deionized water. The microbubbles of the dichlorofluoroethane and trichlorofluoromethane mixture generated via heating gasification are stabilized by the combination with the stabilization agent in the suspension. The preparation method is: 3 g stabilization agent (1.5 g Pluronic F68, 0.5 g phosphatidylethanolamine and 1 g phospholipid) is added into 100 ml hydrogel composed of 0.05% sodium polyacrylate and 0.1% agar, and mixed well. The solution is cooled down by ice cold bath, and dichlorofluoroethane and trichlorofluoromethane mixture in liquid state is added in. Oil-in-water emulsion using dichlorofluoroethane and trichlorofluoromethane mixture as the oil phase is prepared using a homogenizer at the speed of 10000 rpm for 3 min. The emulsion is heated by a water bath at 40° C., and dichlorofluoroethane and trichlorofluoromethane mixture is gasified to form gas microbubbles. Milky microbubbles of dichlorofluoroethane and trichlorofluoromethane mixture-hydrogel suspension is obtained. The CT density of the resulted aqueous negative contrast agent is measured using the method as described in example 1, as well as the pig intestine lumen CT density after filling with the agent. The results are: the CT density of the prepared aqueous negative contrast agent is around −250 HU; the CT density of the pig intestine lumen is decreased to as low as −250 HU. The signals intensities inside the lumen are uniform without visible conglomeration in the CT images.

The invention claimed is:

1. A stable aqueous negative contrast agent for CT imaging of the gastrointestinal tract, wherein said stable aqueous negative contrast agent is a suspension of low CT density gas microbubbles that are coated by one or more stabilization agents and suspended in an aqueous hydrogel matrix, the components including: hydrogel matrix from 0.01 to 1 weight percentage, one or more stabilization agents from 0.1 to 5 weight percentage, and water, the stable aqueous negative contrast agent including the gas microbubbles at a volume concentration in the hydrogel matrix of 5 to 50% at 25° C. under one atmosphere pressure, wherein during use the hydrogel matrix distends the intestinal wall and the microbubbles that are coated by one or more stabilization agents decrease the CT density of the intestinal lumen.

2. The stable aqueous negative contrast agent for CT imaging of the gastrointestinal tract according to claim 1, wherein said suspension has a CT density in the range of −30 HU to −500 HU.

3. The stable aqueous negative contrast agent for CT imaging of the gastrointestinal tract according to claim 1, wherein the matrix of said suspension is formulated as a viscous liquid or semisolid using synthetic or natural hydrophilic polymers dispersed or swelled in water.

4. The stable aqueous negative contrast agent of CT imaging of the gastrointestinal tract according to claim 1, wherein said aqueous hydrogel matrix contains aqueous polymers comprised of: cellulose or derivatives thereof, agar, gelatin, arabic gum, tragacanth, chitosan or derivatives thereof, sodium polyacrylate, and their combinations in different ratios.

5. The stable aqueous negative contrast agent for CT imaging of the gastrointestinal tract according to claim 1, wherein said gas microbubbles comprise air, carbon dioxide, nitrogen, oxygen, fluoroalkanes, chlorofluoralkanes, thiofluroalkanes or inert gas.

6. The stable aqueous negative contrast agent for CT imaging of the gastrointestinal tract according to claim 5, wherein said inert gas is selected from helium, neon, argon, krypton, xenon, or their combination.

7. The stable aqueous negative contrast agent for CT imaging of the gastrointestinal tract according to claim 1, wherein said one or more stabilization agents are selected from at least one of the group consisting of caprolactone, gluconate, ionic and non ionic surfactants, lipids, amphiphilic polymers and their combinations in different ratios.

8. A stable aqueous negative contrast agent for CT imaging of the gastrointestinal tract, wherein said stable aqueous negative contrast agent is a suspension of low CT density gas microbubbles coated by one or more stabilization agents and suspended in an aqueous hydrogel matrix, the components including: hydrogel matrix from 0.01 to 1 weight percentage, one or more stabilization agents from 0.1 to 5 weight percentage, and water, the contrast agent including the gas microbubbles at a volume concentration in the hydrogel matrix of 5 to 50% at 25° C. under one atmosphere pressure, the aqueous hydrogel matrix containing aqueous polymers comprised of: cellulose or derivatives thereof, agar, arabic gum, tragacanth or derivatives thereof, sodium polyacrylate, and their combinations in different ratios, wherein during use the hydrogel matrix distends the intestinal wall and the microbubbles that are coated by one or more stabilization agents decrease the CT density of the intestinal lumen.

9. The stable aqueous negative contrast agent for CT imaging of the gastrointestinal tract according to claim 8, wherein the aqueous hydrogel matrix further contains gelatin, chitosan or derivatives thereof, or their combinations in different ratios.

10. The stable aqueous negative contrast agent for CT imaging of the gastrointestinal tract according to claim 8, wherein said suspension has a CT density in the range of −30 HU to −500 HU.

11. The stable aqueous negative contrast agent for CT imaging of the gastrointestinal tract according to claim 8, wherein the matrix of said suspension is formulated as a viscous liquid or semisolid using synthetic or natural hydrophilic polymers dispersed or swelled in water.

12. The stable aqueous negative contrast agent for CT imaging of the gastrointestinal tract according to claim 8, wherein said gas microbubbles comprise air, carbon dioxide, nitrogen, oxygen, fluoroalkanes, chlorofluoralkanes, thiofluroalkanes or inert gas.

13. The stable aqueous negative contrast agent for CT imaging of the gastrointestinal tract according to claim 12, wherein said inert gas is selected from helium, neon, argon, krypton, xenon, or their combination.

14. The stable aqueous negative contrast agent for CT imaging of the gastrointestinal tract according to claim 8, wherein said one or more stabilization agents are selected from at least one of the group consisting of caprolactone, gluconate, ionic and nonionic surfactants, lipids, amphiphilic polymers and their combinations in different ratios.

15. A method for preparing the aqueous negative contrast agent for CT imaging of the gastrointestinal tract according to claim 1, said method comprising:
adding stabilizing agent to the hydrogel matrix;
adding or preparing the gas microbubbles within the hydrogel matrix; and
uniformly dispersing the gas microbubbles throughout the hydrogel matrix by outside force, so as to obtain the aqueous negative contrast agent for CT imaging of the gastrointestinal tract.

16. The method for preparing the aqueous negative contrast agent for CT imaging of the gastrointestinal tract according to claim 15, wherein said gas microbubbles with low density are generated via feeding a gas stream to the hydrogel and mechanically forcing the gas stream to form the microbubbles.

17. The method for preparing the aqueous negative contrast agent for CT imaging of the gastrointestinal tract according to claim 15, wherein said gas microbubbles with low density are prepared according to a process including
dispersing a fluoroalkane, the chloride or sulphide of an alkane, or their combinations into the hydrogel matrix at a temperature that is below the phase-transition temperature to form an oil-in-water emulsion, and
heating the oil-in-water emulsion to gasify the fluoroalkane, the chloride or sulphide of alkane, or their combinations, and form the microbubbles.

* * * * *